| United States Patent [19] | [11] Patent Number: 4,642,398 |
|---|---|
| Cantrell | [45] Date of Patent: Feb. 10, 1987 |

[54] PREPARATION OF FLUORONITROBENZENE COMPOUNDS IN DISPERSION OF POTASSIUM FLUORIDE

[75] Inventor: Gary L. Cantrell, Belleville, Ill.

[73] Assignee: Mallinckrodt, Inc., St. Louis, Mo.

[21] Appl. No.: 816,481

[22] Filed: Jan. 6, 1986

[51] Int. Cl.$^4$ .............................................. C07C 79/12
[52] U.S. Cl. ...................................... 568/937; 568/938
[58] Field of Search ................. 568/937, 938; 564/417

[56] References Cited

U.S. PATENT DOCUMENTS

| 3,064,058 | 11/1962 | Duesel et al. | 568/937 |
|---|---|---|---|
| 3,240,824 | 3/1966 | Boudakian et al. | 568/937 |
| 3,480,667 | 11/1969 | Siegart et al. | 568/937 |
| 4,069,262 | 1/1978 | Kunz | 568/937 |
| 4,140,719 | 2/1979 | Tull et al. | 568/937 |
| 4,164,517 | 8/1979 | Fuller | 568/938 |
| 4,226,811 | 10/1980 | Oeser et al. | 568/937 |
| 4,229,365 | 10/1980 | Oeser et al. | 568/937 |
| 4,287,374 | 9/1981 | North | 568/938 |
| 4,294,988 | 10/1981 | Tull et al. | 568/938 |
| 4,418,229 | 11/1983 | White | 568/938 |

FOREIGN PATENT DOCUMENTS

| 65226 | 4/1983 | Japan | 568/937 |
|---|---|---|---|
| 13743 | 1/1985 | Japan | 568/938 |
| 2042507 | 9/1980 | United Kingdom | 568/937 |
| 2058067 | 4/1981 | United Kingdom | 568/937 |

OTHER PUBLICATIONS

Finger et al., Journal of the American Chemical Society, 78, 6034–6037 (1956), p. 6035.

Primary Examiner—Stephen J. Lechert, Jr.
Assistant Examiner—Anne Brookes
Attorney, Agent, or Firm—R. G. Jackson; L. N. Goodwin; R. J. Klostermann

[57] ABSTRACT

An improved process is disclosed for preparing fluoronitrobenzene compounds wherein chloronitrobenzene compounds are reacted with potassium fluoride in a solvent dispersion thereof prepared from a mixture including the solvent, the fluoride, methanol and an aromatic compound.

6 Claims, No Drawings

PREPARATION OF FLUORONITROBENZENE COMPOUNDS IN DISPERSION OF POTASSIUM FLUORIDE

BACKGROUND OF THE INVENTION

The present invention relates to an improved process for preparing fluoronitrobenzene compounds wherein chloronitrobenzene compounds are reacted with potassium fluoride in a solvent dispersion thereof prepared from a mixture including the solvent, the fluoride, methanol and an aromatic compound.

Fluoronitrobenzene compounds such as 2-fluoronitrobenzene, 4-fluoronitrobenzene, and 2,4-difluoronitrobenzene, are useful as intermediates for the synthesis of various herbicidal compounds, dyes, and the like. Such compounds have been prepared from corresponding chloronitrobenzene compounds by so-called halogen exchange reactions, illustrated as follows:

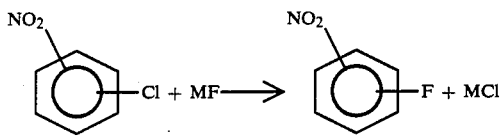

wherein MF represents an alkali metal fluoride salt. The reaction is generally conducted in an aprotic, polar, organic solvent, such as dimethylsulfoxide, dimethylformamide, tetramethylenesulfone (sulfolane), and the like.

Alkali metal fluoride salts are not soluble in such solvents. Therefore, the reaction mixtures usually contain two phases, i.e., solid and liquid phases or two immiscible liquid phases. Finger, et al., *J. Am. Chem Soc.*, 78, 6034 (1956) and Duesel, et al., U.S. Pat. No. 3,064,058 (1962), describe the reaction of chloronitrobenzene compounds with finely-divided, solid potassium fluoride in aprotic polar solvents to produce corresponding fluoronitrobenzene compounds. Boudakian, et al., U.S. Pat. No. 3,240,824 (1966), describe the reaction of o-chloronitrobenzene with solid potassium fluoride at elevated temperatures, without any solvent or diluents, to produce o-fluoronitrobenzene. Napier and Starks, U.S. Pat. No. 3,992,432 (1976), describe a reaction involving two liquid phases. In the Napier and Starks reaction, the inorganic fluoride salt is dissolved in an aqueous phase, and the chloronitrobenzene compound is dissolved in a water-immiscible, organic phase. The reaction is catalyzed by a quaternary salt, which reportedly transfers ions across the phase interface.

Use of quaternary salt phase-transfer catalysts in solid-liquid, two phase reactions also has been known. For instance, Kunz, U.S. Pat. No. 4,069,262 (1978), describes the production of 2-fluoronitrobenzene by reacting 2-chloronitrobenzene with ultrafine particulate potassium fluoride in tetramethylenesulfone solvent using a macrocyclic ether (crown ether) or a quaternary ammonium halide (such as tetrabutylammonium chloride, benzyltrimethylammonium chloride, benzyltrimethylammonium fluoride or benzyltriethylammonium chloride) as the catalyst.

Tull, et al., U.S. Pat. No. 4,140,719 (1979), describes the production of 2,4-difluoro-5-chloronitrobenzene by reacting 2,4,5-trichloronitrobenzene with a solid fluorinating agent selected from NaF, KF, CsF, and $C_{1-4}$ alkyl quaternary ammonium fluoride, and mixtures thereof under substantially anhydrous conditions in the presence of a quaternary compound solid-liquid phase transfer catalyst. The liquid phase comprises an organic solvent in which the trichloro compound is soluble and the fluorinating agent is essentially insoluble.

Starks, "Selecting a Phase Transfer Catalyst," *Chemtech* (February 1980), pages 110-117, describes patterns that purportedly enable prediction of catalysts for anion transfer from aqueous or solid inorganic phases to organic phases.

North, U.S. Pat. No. 4,287,374 (1981) discloses a process for the production of a monofluoronitrobenzene in which a monochloronitrobenzene is heated with an alkali metal fluoride and a phase transfer catalyst at a temperature of no more than 200° C., preferably 125°-170° C., especially 140°-150° C. North discloses, as examples of such catalysts which may be used, long chain alkylammonium halides.

In general, halide-exchange reactions for preparing fluoronitrobenzene compounds by reacting chloronitrobenzene compounds with fluoride salts in aprotic, polar organic solvents in the presence of quaternary ammonium salt phase-transfer catalysts proceed at faster rates when conducted at elevated temperature relative to rates obtainable at lower temperature. However, quaternary ammonium phase-transfer catalysts employed in heretofore known methods are less stable at higher temperature and have been found to decompose or lose their catalytic activity at elevated reaction temperatures. Moreover, U.S. Pat. No. 4,418,229 (to White), incorporated herein by reference, discloses that lower molecular weight catalysts, i.e., those having a total number of carbon atoms less than about 16, are less stable under the conditions (including elevated temperature) of the method of the invention disclosed therein than the therein preferred catalysts of higher molecular weight having about 16 or more carbon atoms.

The above cited White patent discloses the finding that in the conversion of chloronitrobenzene compounds to corresponding fluoronitrobenzene compounds using a quaternary ammonium salt phase-transfer catalyst at elevated temperatures, a high level of catalytic activity can be maintained by adding the catalyst to the reaction mixture incrementally during the course of the reaction.

However, there remains a substantial need in the art for new and improved processes for preparing fluoronitrobenzenes. The present invention substantially fufills such need.

DESCRIPTION OF THE INVENTION

Generally stated, the present invention provides an improved process for preparing a fluoronitrobenzene compound by reaction of a corresponding chloronitrobenzene compound with potassium fluoride in an aprotic polar organic solvent under substantially anhydrous halide-exchange conditions in the presence of a catalyzing amount of a phase-transfer catalyst.

The improvement comprises effecting the reaction in a substantially anhydrous dispersion of ultra-fine particulate potassium fluoride in an aprotic polar organic solvent, said dispersion prepared by a method comprising (a) preparing a solution of potassium fluoride in methanol, (b) preparing a mixture by adding to said solution (i) an aromatic compound selected from aromatic hydrocarbons, aromatic chlorohydrocarbons and aromatic fluorohydrocarbons, said aromatic compound being an azeotrope former with methanol, and (ii) an aprotic polar solvent having a boiling point at a selected pressure at least 30° C. higher than the boiling point at said pressure of said aromatic compound, (c) distilling said mixture at said pressure to prepare a distillation residue consisting essentially of said dispersion.

DETAILED DESCRIPTION OF THE INVENTION AND OF THE MANNER AND PROCESS OF MAKING AND USING IT

Suitable aromatic compounds include for example toluene, benzene, xylene, isopropyl benzene, chlorobenzene and fluorobenzene. Toluene is preferred.

Suitable aprotic polar solvents include for example sulfolane, N-methylpyrrolidone, dimethyl formamide and dimethylsulfoxide. Sulfolane is preferred.

Per gram of crude potassium fluoride there can be used for example about 0.5 to about 0.6 ml of methanol (preferably about 0.55 ml), about 2 to about 3 grams of the aprotic polar solvent (preferably about 2 grams of sulfolane) and about 40 to about 60 ml of the aromatic compound (preferably about 50 ml of toluene).

The aromatic compound preferably is a compound which also forms an azeotrope with water, thereby resulting in removal by the distillation step of water which may be present in the potassium fluoride. Toluene and the other aromatic compounds set forth above each from azeotropes with water.

Although the solution and mixture can be prepared at any suitable temperature, 20°–25° C. is preferred. The solution and mixture are prepared by adding together the respective indicated ingredients with stirring.

Methanol and the aromatic compound (and water if present) are then removed from the resulting mixture in the distillation step.

Distillation is effected at a temperature and pressure effective for removing the methanol and aromatic compound from the mixture. It is critical that the aprotic polar solvent have a boiling point at the distillation pressure (e.g. 760mm Hg) at least 30° C. higher than the boiling point at such pressure of the aromatic compound in order to effect removal of substantially all the aromatic compound and methanol by simple distillation.

The preferred combination of toluene as the aromatic compound and sulfolane as the aprotic polar solvents satisfies this boiling point differential at all pressures up to at least 30 psi.

Distillation is preferably continued until substantially all the methanol, aromatic compound and water (if present) are removed. The distillation pressure is preferably atomspheric or subatmospheric.

Potassium fluoride, which is insoluble in the aprotic polar organic solvent, is precipitated by the distillation step, resulting in formation of the dispersion of substantially anhydrous ultra-fine particulate potassium fluoride in the solvent.

The reaction mixture for the above reaction of chloronitrobenzenes (CNB) with the fluoride can be effected by adding the desired CNB and phase transfer catalyst (PTC) to the dispersion, preferably in the order given and with stirring. The PTC can be any PTC which catalyzes the reaction, such as quaternary ammonium or phosphonium salts having known catalytic utility therefor.

The halide-exchange conditions generally include elevated reaction temperatures, which are high enough to provide sufficient energy of activation for the reaction. Although such reaction temperatures might cause some catalyst inactivation, the temperature is preferably not so high as to cause rapid decay of catalytic activity or substantial decompostion of the reactants, the products, or the solvent. Although the reaction temperature may vary, depending upon the particular catalyst, solvent, and reactants used, generally it may be, for example, from about 120° C. to about 220° C., preferably from about 160° C. to about 215° C., and more preferably from about 205° C. to about 215° C.

Those skilled in the art will appreciate that a variety of equipment and techniques may be utilized in the method of the present invention, and the invention is not limited to any particular equipment or technique. The method is generally conducted by charging the reactants, solvent and PYR salt catalyst into a reaction vessel which is equipped with agitating and heating means. Advantageously, the entire amount of the reactants, solvent and PTC salt catalyst to be employed can be added initially. The reaction vessel may also advantageously include a reflux condenser or other means of recovering solvent vapors and means for blanketing the reaction mixture with a dry inert gas, e.g., nitrogen. The reaction mixture is heated to the desired reaction temperature and agitated.

The halide-exchange reaction conditions employed in the present invention advantageously include substantially anhydrous reaction conditions. The presence of water in the reaction can diminish yields and result in undesirable by-products. Various techniques may be used for dehydrating the reactants and solvent, such as vacuum drying, azeotropic distillation, chemical drying and the like. Azeotropic distillation, for example with benzene, can be used for drying all of the reactants and solvents; however, any convenient and operable technique may be employed. Due to the deleterious effect of water, the reaction mixture is preferably substantially devoid of water. Small amounts of water may be tolerated; however, a corresponding reduction in yield is generally experienced. Advantageously, the concentration of water in the reaction mixture is below about 5 wt. % and is preferably below about 1 wt. %, based on the weight of the reaction mixture.

The solvent for the catalyst, chloronitrobenzene compound, and fluoronitrobenzene compound is an aprotic, polar, organic solvent, which preferably has a relatively high boiling point, e.g., a boiling point above about 190° C. Lower boiling solvents may be used; however, pressure reactors may be required for their containment. Solvents having boiling points below a desired reaction temperature may be employed by conducting the reaction under superatmospheric pressure in such reactors. Examples of reaction solvents include dimethylsulfoxide, sulfolane, bis(2-methoxyethyl)ether, bis 2-(2-methoxyethoxy) ethyl ether, hexamethylphosphoramide, N-methylpyrolidinone, and dimethylformamide. Dimethylformamide and sulfolane are preferred solvents. Sulfolane is most preferred from the standpoint of commercial attractiveness.

The phase-transfer catalyst employed in the present method is soluble in the reaction solvent in an amount sufficient to catalyze the reaction. The PTC salt may be employed in any catalyzing amount, i.e., in any amount effective for catalyzing the conversion of the chloronitrobenzene compound to the corresponding fluoronitrobenzene compound. In general, the amount may correspond, for example, to a molar ratio of PTC salt to chloronitrobenzene compound of from about 0.005:1 to about 0.5:1, preferably from about 0.04:1 to about 0.15:1, most preferably about 0.08:1. In general, amounts of PTC salt corresponding to molar ratios of less than about 0.005:1 may not provide sufficient catalytic activity, while amounts corresponding to molar ratios of more than 0.5:1 may result in insufficient additional benefit to justify the additional cost. As indicated above, the entire amount of PTC salt to be used is preferably added initially. However, if desired, a portion may be added initially with incremental addition of the remainder during the course of the reaction. Incremental addition may be, for example, substantially in accordance with the invention disclosed in the above-cited White patent.

The fluoride ion is provided by an alkali metal fluoride salt which is generally present in an amount at least substantially stoichiometric to the chloronitrobenzene reactant. Preferred fluoride salts are potassium fluoride, rubidium fluoride, and cesium fluoride, and potassium fluoride is particularly preferred. The fluoride salt is advantageously finely-divided, to provide a greater superficial surface area which is accessible to the catalyst and the chloronitrobenzene compound. Preferred concentrations of the fluoride salt range from about 1 to about 2 times the stoichiometric amount, most preferably from about 1.2 to about 1.6 times such amount. For example, in a method for producing a monofluoronitrobenzene compound, a preferred molar ratio of fluoride salt to chloronitrobenzene compound is about 1.5:1. Lower concentrations of fluoride salts can result in diminished reaction rates, and, although higher concentrations can be used, no appreciable benefit is generally realized therefrom. In the chloronitrobenzene compound used as a starting material in the present invention, the relative positions of the nitro and chloro substituents, and the presence of other substituents on the ring can affect the reactivity of the starting compound. Generally, halogen exchange reactions involve compounds in which the chloride is in the ortho or para position with respect to the nitro group, and reactivity may increase when other electron-withdrawing groups are present on the ring. Compounds having chloro substituents in the meta as well as ortho and/or para positions may be used as starting materials, but usually only the chloro groups in the ortho and para positions will undergo halogen exchange. Accordingly, the method of this invention may be used for example for the synthesis of compounds such as 2-fluoronitrobenzene, 2-fluoro-3-chloronitrobenzene, 4-fluoronitrobenzene, 2,4-difluoronitrobenzene, 5-chloro-2,4-difluoronitrobenzene, and the like, from corresponding chloronitrobenzene compounds. The present method is particularly useful for the preparation of 4-fluoronitrobenzene from 4-chloronitrobenzene and 2-fluoronitrobenzene from 2-chloronitrobenzene.

The reaction is generally allowed to proceed until substantially all the chloronitrobenzene compound has been converted to the corresponding fluoronitrobenzene compound. A reaction time of from about 10 minutes to about 20 hours may typically be used, and the reaction will often be substantially complete after about 1 to about 6 hours. After the reaction is completed, the product can be recovered by any suitable procedure, such as extraction, distillation, steam distillation and the like. For some purposes, the purity of the crude reaction product, recovered as an organic phase after addition of water to the reaction mixture, will be satisfactory.

The method of this invention has been found to produce fluoronitrobenzene compounds in good yields with little formation of by-products.

Practice of this invention is further illustrated by the following non-limiting examples. All parts, percents and other amounts throughout this disclosure are by weight unless otherwise indicated.

The N-(2-ethylhexyl)-4-(N',N'-dimethylamino)-pyridinium chloride salt employed in the following examples can be prepared in accordance with the procedure described by Brunelle in U.S. Pat. No. 4,460,778, incorporated herein by reference. As described therein, a mixture of 12.217 grams of dimethylaminopyridine, 20.833 grams of 2-ethylhexylmethane sulfonate was stirred and heated at 110° C. for 1 hour. There was added to the resulting mixture 25 grams of toluene and the solution was refluxed for an additional hour. Toluene was then removed from the mixture under reduced pressure and the resulting crude mesylate salts were washed with hexane. The mesylate salts were then dissolved in the methylene chloride and washed twice with a saturated sodium chloride solution. Methylene chloride was then removed under reduced pressure from the resulting product. There was obtained 31.728 grams of a product having a melting point of 189°–190° C. Based on method of preparation, the product was N-2-ethylhexyldimethylaminopyridine chloride (EHD-MAPC).

EXAMPLE

To a 250-ml reaction vessel equipped with a stirrer, thermometer and reflux condenser were added 27.5 grams of commercially available potassium fluoride containing approximately 1 to 5% water and 50 ml of methanol. The resulting mixture was refluxed for one half hour, thereby dissolving the potassium fluoride in methanol. To the resulting solution at about 64° to 67° C. was added with stirring 55.2 grams of sulfolane, followed by adding 50 ml of toluene with stirring. Next, substantially all the toluene and methanol were removed by distillation at atmospheric pressure and 64°–110° C., followed by heating at 160° C. under subatmospheric pressure (approx. 200 mm Hg absolute pressure). There was obtained a dispersion of finely divided particulate potassium fluoride in sulfolane, which was judged to be substantially free of water (i.e. not containing more than about 0.5% water based on the weight of the potassium fluoride).

The dispersion was cooled to 100° C. (for additional safety in making the following additions). Then p-chloronitrobenzene (50.3 grams, 0.319 mole) was added, followed by adding N-2-ethylhexyl-4-(N',N'-dimethylamino)pyridinium chloride (0.6 gram, 0.0022 mole). The resulting reaction mixture was heated to 210°–215° C. While maintaining the reaction mixture at such temperature and with stirring, the progress of the reaction was followed by sampling the reaction mixture from time to time. Each sample was analyzed by high pressure liquid chromatography (HPLC) using a Waters Bondapak ™ C18 reverse phase column, a 2-microliter sample loop, a UV detector at 254 nanometers and a dual pump. The solvent system was a 1:1 mixture of the flows from pump A (1:1 methanol:water) and pump B (methanol). The combined flow rate was 1.5 microliters per minute. For each sample, the peak area of the resulting fluoronitrobenzene was measured using a digital integrator. Results are shown below:

| TIME, HOURS | AREA PERCENT OF 4-FLUORONITROBENZENE |
|---|---|
| 1.0 | 45.4 |
| 4.0 | 87.9 |
| 5.0 | 92.7 |

At the end of 5 hours or more, the resulting para-fluoronitrobenzene product can be recovered in approximately 85% or more yield by discontinuing heating and removing the product as distillate by simple distillation under increasingly lower pressure (to about 100 mm Hg absolute), while heating as necessary to maintain an acceptable distillation rate (e.g. at a temperature of the mixture of approximately 135°-150° C.

Experience has shown that under the same conditions except that the above treatment of the potassium fluoride is omitted, as best a 50% conversion of p-chloronitrobenzene to p-fluoronitrobenzene is obtainable.

BEST MODE CONTEMPLATED

The best mode contemplated for carrying out this invention has been set forth in the above description, for example, by way of setting forth preferred materials and operating conditions, including but not limited to preferred ranges and values of amounts and other non-obvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. In a process for preparing a fluoronitrobenzene compound by reaction of a corresponding chloronitrobenzene compound with potassium fluoride in an aprotic polar organic solvent under substantially anhydrous halide-exchange conditions in the presence of a catalyzing amount of a phase-transfer catalyst,
   the improvement which comprises effecting the reaction in a substantially anhydrous dispersion of utlra-fine particulate potassium fluoride in an aprotic polar organic solvent, said dispersion prepared by a method comprising
   (a) preparing a solution of potassium fluoride in methanol,
   (b) preparing a mixture by adding to said solution (i) an aromatic compound selected from aromatic hydrocarbons, aromatic chlorohydrocarbons and aromatic fluorohydrocarbons, said aromatic compound being an azeotrope former with methanol, and (ii) an aprotic polar solvent having a boiling point at a selected pressure at least 30° C. higher than the boiling point at said pressure of said aromatic compound, and
   (c) distilling said mixture at said pressure to prepare a distillation residue consisting essentially of said dispersion.

2. The process of claim 1 wherein said aromatic compound is selected from the group consisting of toluene, benzene, xylene, isopropyl benzene, chlorobenzene and fluorobenzene.

3. The process of claim 2 wherein said compound is toluene.

4. The process of claim 1 wherein said aprotic polar solvent is selected from the group consisting of sulfolane, N-methylpyrrolidone, dimethyl formamide and dimethylsulfoxide.

5. The process of claim 4 wherein said solvent is sulfolane.

6. The process of claim 1 wherein said potassium fluoride from which said solution is formed contains a minor amount of water, said aromatic compound additionally forms an azeotrope with water, and said distillate contains substantially all the water initially contained in said solution.

* * * * *